(12) United States Patent
Shorte et al.

(10) Patent No.: US 7,738,695 B2
(45) Date of Patent: Jun. 15, 2010

(54) METHOD AND DEVICE FOR 3 DIMENSIONAL IMAGING OF SUSPENDED MICRO-OBJECTS PROVIDING HIGH-RESOLUTION MICROSCOPY

(75) Inventors: Spencer Shorte, Orsay (FR); Torsten Müller, Berlin (DE); Thomas Schnelle, Berlin (DE)

(73) Assignees: Institut Pasteur, Paris (FR); PerkinElmer Cellular Technologies Germany GmbH, Hamburg (DE)

( * ) Notice: Subject to any disclaimer, the term of this patent is extended or adjusted under 35 U.S.C. 154(b) by 887 days.

(21) Appl. No.: 10/532,147

(22) PCT Filed: Oct. 24, 2003

(86) PCT No.: PCT/EP03/11818

§ 371 (c)(1),
(2), (4) Date: Oct. 20, 2005

(87) PCT Pub. No.: WO2004/038484

PCT Pub. Date: May 6, 2004

(65) Prior Publication Data

US 2006/0126921 A1 Jun. 15, 2006

(30) Foreign Application Priority Data

Oct. 25, 2002 (EP) .................................. 02292658

(51) Int. Cl.
*G06K 9/00* (2006.01)
(52) U.S. Cl. ...................... 382/154; 382/128; 382/129; 382/284; 345/418; 345/419; 345/420; 356/336; 356/335; 356/337; 356/343; 356/904

(58) Field of Classification Search .................. 382/154, 382/129, 285; 359/368, 676, 738; 436/524, 436/526; 435/7.1; 219/121.68; 210/645, 210/732; 345/418, 419, 420
See application file for complete search history.

(56) References Cited

U.S. PATENT DOCUMENTS 5,620,857 A * 4/1997 Weetall et al. ............... 435/7.1

(Continued)

FOREIGN PATENT DOCUMENTS

DE 197 57 785 A1 7/1999

(Continued)

OTHER PUBLICATIONS

Automated electrorotation: dielectric characterization of living cells by real-time motion estimation, De Gasperis et al, 1998.*

(Continued)

*Primary Examiner*—Wesley Tucker
*Assistant Examiner*—Nancy Bitar
(74) *Attorney, Agent, or Firm*—Caesar, Rivise, Bernstein, Cohen & Pokotilow, Ltd.

(57) ABSTRACT

A method for high-resolution image recording of at least one object with a microscope, includes the steps of: (a) positioning the object in a receptacle being arranged in the optical axis of the microscope, (b) generating at least two first data sets per object which represent intermediate images of the object with at least two different orientations relative to the optical axis of the microscope, wherein the different orientations of the object are provided by moving the object relative to the receptacle, and (c) evaluating the data sets for obtaining quantitative three dimensional information.

21 Claims, 7 Drawing Sheets

U.S. PATENT DOCUMENTS

| | | |
|---|---|---|
| 5,948,328 A | 9/1999 | Fiedler et al. |
| 6,440,285 B1 * | 8/2002 | Fuhr .......................... 204/457 |
| 6,663,757 B1 * | 12/2003 | Fuhr et al. .................. 204/450 |
| 6,678,413 B1 * | 1/2004 | Liang et al. ................. 382/181 |
| 6,801,311 B1 * | 10/2004 | Fuhr et al. .................. 356/336 |
| 6,891,671 B1 * | 5/2005 | Greenberg .................. 359/388 |
| 6,991,906 B1 * | 1/2006 | Fuhr et al. ................... 435/7.1 |
| 7,081,192 B1 * | 7/2006 | Wang et al. ................. 204/547 |
| 7,161,741 B1 * | 1/2007 | Schaack ..................... 359/676 |
| 7,211,804 B2 * | 5/2007 | Yoshida et ............. 250/396 R |
| 7,312,085 B2 * | 12/2007 | Chou et al. ................... 436/43 |
| 7,419,576 B1 * | 9/2008 | Hata .......................... 204/603 |
| 7,501,233 B2 * | 3/2009 | Gradl et al. ..................... 435/4 |
| 2002/0050988 A1 * | 5/2002 | Petrov et al. ................. 345/418 |
| 2007/0119714 A1 * | 5/2007 | Schnelle et al. ............. 204/547 |

FOREIGN PATENT DOCUMENTS

| | | |
|---|---|---|
| DE | 199 03 001 A1 | 8/2000 |
| EP | 0 517 454 A2 | 12/1992 |
| WO | WO 96/24875 A1 | 8/1996 |
| WO | WO 00/37920 A1 | 6/2000 |

OTHER PUBLICATIONS

'Strategy for far-field optical imaging and writing without diffraction limit' Physics Letters A vol. 326, 2004, pp. 140-145; 2004.*

Trapping in AC octode field cages; Th. Schnelle, Müller and G. Fuhr; 2000.*

Combined laser tweezers and dielectric field cage for the analysis of receptor-ligand interactions on single cells Christoph Reichle et al; 2001.*

Micro Rotation Imaging DEconvolution, Saux et al.2008.*

Chalmond, B., et al., in "Inverse Problems" vol. 15, pp. 399-411 (1999).

Fuhr, G., et al., "Biochim. Biophys. Acta" 1108, pp. 215-223 (1992).

Fuhr, et al., "Appl. Phys. A." 67, pp. 385-390 (1998).

Müller, Th., et al., "Biosensors & Bioelectronics" 14, pp. 247-256 (1999).

Müller, Th., et al., "European Biophysics Journal" 29/4-5 (2000).

Reichle, Ch., et al., "Biochim. Biophys. Acta" 1459, pp. 218-229 (2000).

Reichle, Ch., et al., "Electrophoresis" 22/2, pp. 272-282 (2001).

Schnelle, Th., et al., "J. Electrostatics" 46, pp. 13-28 (1993).

Schnelle, Th., et al., "J. Electrostatics" 50, pp. 17-29 (2000).

Schnelle, Th., et al., "Appl. Phys. B" 70, pp. 267-274 (2000).

Schnelle, Th., et al., "Electrophoresis" 21, pp. 66-73 (2000).

Wissel, H., et al., "American Journal of Physiology Lung Cell Mol. Physiol." 281, pp. L345-L360 (2001).

* cited by examiner

METHOD AND DEVICE FOR 3 DIMENSIONAL IMAGING OF SUSPENDED MICRO-OBJECTS PROVIDING HIGH-RESOLUTION MICROSCOPY

The invention is related to methods and devices for high-resolution image recording of at least one object, in particular with a microscope.

1) THE BACKGROUND OF THE INVENTION

A) Microscopy—in Biological Research.

The development of fluorescent bio-molecular probes—especially fluorescent proteins enabling the observation of sub-cellular process and structure inside living cells, has come to pass as a renaissance in light microscopy. Now a variety of evolving bio-chemical techniques incorporate and/or are based upon combining fluorescent molecular probes and light microscopy. They provide both qualitative and quantitative visualization of specific molecular dynamics underlying live cellular activities. However, inasmuch as it is now clear that these biological processes depend upon spatio-temporal compartmentalization, the major focus for development in light microscopy, is to overcome certain systematic problems that obstruct our ability to render simple, yet quantitatively accurate three-dimensional mapping of fluorescent signals inside living cells (viz. 3-D microscopy).

Three Major Systematic Problems in 3-D Microscopy

The ability to render three-dimensional maps of fluorescent signals from micro objects visualized by light microscopy is limited mainly by three systematic artifacts.

a) Axial Aberration—the Elongation Effect

Figure 9:
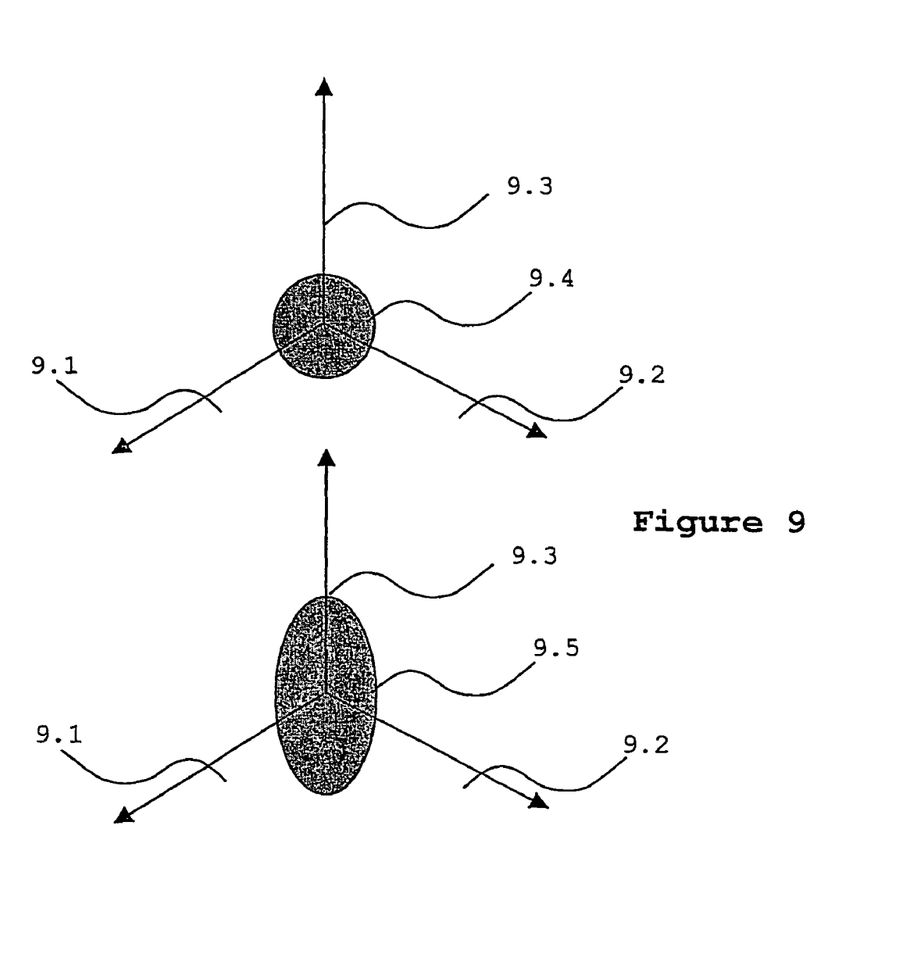
FIG. 9: an illustration of the elongation effect in conventional microscopes.

A central issue in light microscopy arises from limitations due to the spatial resolution of images. This is dependent upon the objective lens used and the geometry of the light focused by the lens. In general, microscope objectives with a high magnification and a high numerical aperture are used for achieving the best resolution (e.g. 63×; 100×/N.A. 1.4 oil immersion). However, there exist physical limitations for light collection through the glass lens of any objective. In particular, the xy resolution is always (at least two times) greater than in the z-axis (a.k.a "optical" axis). Specifically, x,y plane resolution is around 100-150 nm, whereas the resolution along the z-axis is much lower (around 300 to 500 nm), and this fact results in a major systematic artifact of light microscopy—i.e. "axial aberration", whereby a spherical object at the focus of a microscope objective in fact appears to be elliptic in shape, with its largest extension along the z-axis, i.e. the light path. A schematic representation of this type of optical aberration (the "elongation" effect) is shown in FIG. 9. The axes of the microscope optics are x (9.1), y (9.2) and z (9.3). A feature 9.4 which is originally circular in reality appears to be elongated 9.5 due to optical aberration, and this problem is one of the major obstacles to overcome in 3 dimensional imaging microscopy.

b) Chromatic Aberration—Axial Misalignment of Multiple Wavelengths.

In addition to the problems of optical aberration and diminished axial resolution that reduce the ability to visualize in 3-D on a light microscope, another problem is referred to as "chromatic aberration" or "axial chromatic aberration". Chromatic aberration occurs in applications where multi color images are acquired (Beyer). When performing z-scans at different wavelengths the light diffraction at the glass-to-medium-interface and within the whole microscope set-up depends upon the wavelength. As a consequence the focus for different wavelengths varies as a function of the z-axis displacement. Various types of correction are used to overcome chromatic aberration, for example, in confocal-microscopy (see below) a calibration of the "zero" position (unique to just one z-axis position) for all colors can be performed by an alignment of the light paths for the different wavelengths using multi colored (artificial) spatial-calibration samples (so-called "Focal Check Microparticles"). However, inasmuch as the calibration is unique to just one z-axis focal position, if a shift in focus occurs a systematic misalignment will again persist.

c) Out of Focus Light, and Diffraction Effects.

The third problem of three-dimensional fluorescence microscopy is that the micro-object itself comprises a complex three-dimensional form, and as such interferes with image visualization from the focal plane. This fact gives rise to a host of related problems for which there is no single general solution. Nonetheless, these problems are inextricably linked and must be considered critically in order to achieve true three-dimensional rendering. In general, these problems stem from light distortion caused by both the object itself, and the non-linear characteristics of light diffusion between different focal planes. These sorts of problem become critical in fluorescence microscopy where so-called "out-of-focus-light", (light from parts of an object laying outside the focal plane) contribute to what is observed at the focal plane. This light compromises the crispness of the image, inasmuch as it introduces an out-of-focus "haze" into the image focal plane.

There are two ways of eliminating or reducing out-of-focus haze: i) confocal microscopy (see below), and ii) deconvolution. The latter is a calculation-intensive, algorithm-based mathematical method for sharpening images (from any source) that contain out-of-focus light. In general, the method requires that an axial stack of images be collected from the sample, at small (e.g. 50-500 nm) steps. The axial stack may then be processed using special algorithms that take into account a variety of optical parameters including the objective lens, and excitation/emission wavelengths. The corrected stack of images is then converted into a three-dimensional model of the object by either removing or reassigning the identified out-of-focus light (Egner, Markham). Using adequate graphics computing power, this three-dimensional model may then be rendered into animations allowing the object to be observed from any arbitrary viewing point.

Disadvantages of this approach are that it is calculation intensive (which costs time and processing power), and that it suffers inaccuracies and artifacts due to its extensive dependence upon calculation-based assumptions and/or corrections that must be applied at multiple stages during the processing procedure. It must also be noted that the best types of deconvolution algorithm rely upon prior measurement of a so-called PSF (Point-Spread-Function) specific to any given optical configuration (ie the microscope set-up). Put simply, the PSF is a measure of light diffusion from a sub-resolution point within a given focal plane, and can therefore be used to "re-map" out-of-focus light back into its appropriate 3-D voxel. However, a major problem with applied algorithms using PSF, is that it is extremely difficult to measure a "good" PSF. In particular, a major problem arises from the fact that the PSF in any given sample is itself altered as a function of the axial distance through the sample (Sedat). This fact results in any single PSF being representative only of a single focal plane, and therefore distorts reconstructions based upon z-axis stacks where clearly the z-axis is deflected in order to scan throughout the volume of a given sample. Finally, in addition to out-of-focus light, the sample (as stated above) alters the diffusion of light through its own volume by diffraction. This gives rise to a further group of problems, whereby light emission from the focal plane is deteriorated due to shading or diffraction do light by optically dense regions within the object itself (e.g. cell) that lay in between the microscope lens and the fluorescent features being imaged.

Advanced Techniques for Improved 3-D Fluorescence Microscopy

Three-dimensional imaging of micro objects requires that the above problems be addressed, and this may in part be achieved using numerous types of novel approach. Herein, a brief description summarises some of the advanced microscope techniques at the cutting edge of what is currently available. However, it should be noted that all will be improved substantially by the utility of the invention described herein. On this point, as for conventional fluorescence microscopy, all these techniques (without exception) achieve 3-D rendering by mechanically scanning the focus through multiple z-axis acquisitions at small (nm) intervals, collected from the sample volume. As such the micro object must, therefore, be immobilized by adherence to an optically transparent surface substrate (normally a 150 micron thick glass cover-slip). The resulting image "z-stack" must then be treated by calculation-intensive processing to yield 3-D rendering.

Single-photon excitation confocal fluorescence microscopy uses focused laser light for fluorescence excitation and, in general, a pinhole in the path of fluorescence emission, which allows in focus light derived from the x,y image plane to pass, but effectively rejects out-of-focus light. Fluorescence light measured using pinhole systems is detected using photo-multipliers and a scanning device. By way of an alternative, some commercial confocal systems use a so-called "Spinning-Disc" (Nipkow disk) system that achieves much the same result by rejecting out-of-focus light. However, the detection system differs inasmuch as it comprises a CCD camera, affording greater speed of acquisition. Either way, the advantage of confocal microscopy is that out-of-focus haze is greatly reduced, and by performing a z-scan, stacks of confocal images can be generated from a sample volume, in order to build a three-dimensional rendering of the imaged volume. Note that this approach still suffers from chromatic and axial aberration problems.

Multi-Photon Excitation Confocal Fluorescence Microscopy

A method for improving resolution in fluorescence microscopy is based upon the use of multi photon laser excitation. Fluorescence excitation of a fluorophore occurs at a certain wavelength λ nominally determined by its specific excitation absorption maxima. Efficient absorption of a single photon at this wavelength results in excitation and emission of fluorescent light (conventional fluorescence microscopy). However, excitation may also be achieved by simultaneous absorption of two photons of lower energy, displaying wavelengths approximately half the excitation maxima. This mode of so-called "multiphoton" excitation is considered to be "biphotonic or two-photon" induced fluorescence, and is made possible by grace of high energy pulsed lasers. In general this mode of excitation can be considered a means to excite fluorescence from, for example, a blue-green absorbing fluorophore using multi-photon excitation from a near-infra-red laser emitting sub-microsecond pulses of light. Inasmuch as the two photons of near-IR light are aligned and collide only at the focal plane of the optical set-up, the energy density of this multi photon excitation is concentrated solely at a single femtoliter volume within the microscope's focal plane. As such, multi-photon excitation is intrinsically confocal by nature. In effect this approach gives a pure, and efficient image free from "out of focus" fluorescence. The disadvantage of multi photon fluorescence microscopy is the requirement for high energy pulsed lasers to be attached to the microscope, resulting in high cost and large, difficult to manage equipment assemblage, maintenance and application.

4Pi Confocal (Theta) Microscopy, Standing-Wave Microscope (SWM), Incoherent Illumination Interference Image Interference Microscopy (I5M)

The generation of higher resolved three-dimensional images of cells can be improved by a combination of the techniques mentioned above and modifications of the opto-mechanic set-up. The use of two separate objective lenses for excitation and collection of fluorescence emission light leads to a smaller detection volume element and an equilateral resolution some 4 times higher than for conventional fluorescence microscopy (Egner). This technique is used in combination with multi photon fluorescence microscopy. In a 4Pi confocal fluorescence microscope two opposing microscope objective lenses are used to illuminate a fluorescent object from both sides and to collect the fluorescent emissions on both sides. Constructive interference of either the illumination wave fronts in the common focus or the detection wave fronts in the common detector pinhole results in an axial resolution approximately four times higher than in a confocal fluorescence microscope (Hell). The excitation/observation volume can be considerably decreased when the detection axis is rotated by an angle Theta (e.g. 90°) relative to the illumination axis as in Theta Microscopy (Lindek). Both methods bring along substantial limitations for the sample carrier and the microscope objective, which can be used. In addition there is a huge effort involved when aligning the two focal volumes of the objective lenses, which has to be done with sub-micrometer precision.

B) Micro Electrode/Fluidics Chamber(s) for Three Dimensional Manipulation of Micro Objects Holding and lifting micro objects by negative dielectrophoresis in a well defined electric field minimum has been described since 1992 (Fuhr, G. et al. "Biochim. Biophys. Acta" 1108, 1992, 215-223). First, planar two-dimensional arrangements of micro electrodes have been used. They contained for example four electrodes with a tip-to-tip distance of 100 to 200 micrometers. Holding and lifting objects in these so-called "field traps" was only possible using alternating fields. Rotational fields had only limited trapping efficiency and were very sensitive to hydrodynamic streaming (Schnelle, Th. et al. "J. Electrostatics" 46, 1993, 13-28, Schnelle, Th. et al. "J. Electrostatics" 50, 2000, 17-29, Schnelle, Th. et al. "Appl. Phys. B" 70, 2000, 267-274, Reichle, Ch. et al. "Biochim. Biophys. Acta" 1459, 2000, 218-229). The development of so-called CellProcessors—three-dimensional electrode arrangements led to "field cages" consisting of eight electrodes and building up closed electric field cages (Schnelle, Th. et al., 1993, see above, Müller, Th. et al. "Biosensors & Bioelectronics" 14, 1999, 247-256, Reichle, Ch. et al. "Electrophoresis" 22/2, 2001, 272-282). "Cell Processors" containing dielectric field cages (DFCs) have been used in combination with a variety of high resolution optical techniques applied to micro objects, such as fluorescence correlation spectroscopy (FCS, Schnelle, Th. et al. "Electrophoresis" 21, 2000, 66-73), force measurements using laser tweezers (Fuhr et al. "Appl. Phys. A." 67, 1998, 385-390), electro-rotation (Schnelle et al., see above), measurement of ligand-receptor binding forces (Reichle et al. 2001, see above) and confocal laser scanning microscopy (Müller, Th. et al. "European Biophysics Journal" 29/4-5, 2000, 12D-3 (Poster); Wissel, H. et al. "American Journal of Physiology Lung Cell Mol. Physiol." 281, 2001, L345-L360).

2) OBJECT OF THE INVENTION

The object of the invention is to provide improved high-resolution measuring methods, in particular imaging methods avoiding the disadvantages of conventional methods. It is a particular object of the invention to provide a generally applicable solution that enhances high-resolution 3-D imaging methods by overcoming, diminishing or avoiding completely the systematic artifacts of light based microscopy described above. The invention shall provide an altogether new approach for the generation of three-dimensional image series describing both quantitatively and qualitatively a more accurate spatial map of any given fluorescent, bioluminescent, or auto-fluorescent micro-object—e.g. a live mammalian cell labelled with fluorescent molecules. Another object of the invention is to provide a device that may be implemented to any (and all) existing fluorescent microscope techniques (as described above).

3) SUMMARY OF THE INVENTION

Generally, the high-resolution image recording according to the invention comprises a positioning of at least one object in a receptacle in the optical axis of a microscope imaging system, generating at least two intermediate images of the object with different orientations in space and evaluating an object image from the intermediate images, wherein the different orientations of the object are provided by moving the object as such relative to the receptacle. The feature of moving only the object while the imaging system and the receptacle are kept at fixed positions (e.g. in a laboratory system) has the advantage of providing high-resolution images without troublesome changes of the opto-mechanical features of the imaging system. The term different orientation refers generally to different geometrical arrangements of the object relative to the optical axis. The arrangements can be obtained by translations and/or rotations.

The invention can avoid completely (1 and 2), or minimize (3) the following problems in 3-D light microscopy:
1. Axial aberration—Elongation effect of the imaged features.
2. Chromatic aberration—axial misalignment at multiple wavelengths.
3. Shading/Diffraction effects due to optically dense regions, and The invention also optimizes completely (4 and 5), and enhances greatly (6) the following procedures of 3-D light microscopy:
4. 3-D object rendering—facile 3-D characterization, NO CALCULATION NEEDED.
5. PSF based algorithm remapping of "haze"—PSF required from single voxel only.
6. Optical Resolution—by using sampling from only one x,y plane to detect axial shape distribution One basic idea of the invention described herein is to use in particular a DFC in order to freely translate and/or rotate the micro object itself in order to record different image planes and to keep the measurement volume itself motionless (or to move it in just one dimension e.g. scanning).

In the context of the current invention these movements of the micro object—e.g. a live suspended biological cell—are preferably realized by time dependent ac electric fields and negative dielectrophoretic forces. They are preferably generated in fluidic micro-chips containing DFC's that are customized to achieve specific movements of the micro object in three dimensional space. In this context we have implemented and substantiated that a DFC comprising eight micro electrodes forming a closed field cage, provides sufficient stability and control to achieve these movements. Ideally, the dimensions—diameter and distance between electrodes—are preferentially within the range of the object's size, i.e. between 1 and 1000 µm. The electrodes were fixed within a microfluidic chamber which was made of a transparent material suitable for high resolution microscopy, e.g. glass with 150 µm thickness. Negative dielectrophoresis was induced by applying electric ac fields in a frequency range of 100 kHz to 100 MHz. Field cages were generated, for example, by applying rotational fields to the two planes of four electrodes each with a phase shift of 90° between the electrodes within one plane and of 180° between the planes. During micro object rotation this mode yielded an efficient dielectric field cage and highly stable positioning in x-, y- and z-directions.

Thus, the invention is based on this surprising and unexpected result of the inventors according to which micro-objects suspended in a fluid can be manipulated with electric field forces with a precision sufficient for an evaluation of the object image from the intermediate images. The precision of rotation even was obtained despite asymmetry and/or gravitation effects. Thus, it has been found that the object can be positioned stably in x-, y- and z-directions. It can be rotated around a defined axis and oriented by addressing the electrodes with a suited signal characterized by time dependent amplitude, frequency and phase.

The physical reason for the rotation of a micro object is a polarization of its charges/dipoles within a rotational field. The torque is dependent upon the field strength, the field frequency and the passive electric properties of the object in relation to the suspending medium. The torque can be deliberately induced by using appropriate rotational fields, i.e. certain phase shifts between the electrodes and/or a certain geometry of the electrode arrangements. Computer/user controlled protocols will be adapted that allow the electrodes to be alternately triggered in order to achieve fixed protocols of micro object movement, and facile directional and speed control. The resulting device shall be capable of allowing the user to select and change the rotational axis, speed of rotation, and extent/angle of deflection.

With this device rotating the object can be realized in a continuous fashion or for defined time periods and angles. For example, a horizontal rotation can be changed to a vertical rotation or a "random" rotation while maintaining the same z-position. Small changes of the rotational axis can be achieved by varying the amplitude and/or the phase at least at a single electrode. Moreover, a well-defined variation of the z-position can be achieved by varying the amplitude and/or the phase within one electrode plane, and rotational axes can be changed without affecting the positioning stability.

For caging objects within a DFC without inducing a torque AC fields can be used. The dipole moment in z is then zero and forcing in z-direction—i.e. the positioning along the z-axis against the force of gravity—is achieved merely by higher moments, e.g. quadruple moment. This works best for a ratio of object diameter compared to tip-to-tip distance of the DFC electrodes of 1:4 to 1:10. Preferred field modulations are adapted for changing a horizontal rotation to a vertical rotation or a "random" rotation while maintaining the same z-position, applying small changes of the rotational axis—typically 1° to 10°—by varying the amplitude and/or the phase at least at one electrode, or varying the z-position—typically 50 nm to 10 μm—by varying the amplitude and/or the phase within one electrode plane. If the object to be investigated has an asymmetrical shape, the electrodes can be controlled such that the object is rotated relative to a fixed centre of rotation. A variation of angular velocity and/or centre of rotation can be compensated by a field amplitude modulation. In terms of a homogeneous compensation, the electric field forces preferably are generated by a plurality of electrodes (about 8 or more) surrounding the object.

According to an alternative embodiment of the invention the micro object may be moved by holding the object at a fixed position by means of electric field forces and by rotating the object by means of optical forces as generated e.g. with laser tweezers.

Image Series Generated from Micro Object Rotation Using the Invention Contain Characteristic 3-D Spatial Information that is Free from Artifacts.

Generally, the high-resolution image recording according to the invention comprises a positioning of at least one object in a receptacle in the optical axis of a microscope imaging system, generating at least two intermediate images of the object with different orientations in space and evaluating an object image from the intermediate images, wherein the different orientations of the object are provided by moving the object as such relative to the receptacle. Clearly, rotating a micro object while maintaining the imaging system, optics and sample receptacle in a fixed position has the advantage of generating an x,y image series that reveals implicitly 3-D details that are transiently axial to the focal plane, but without axial or chromatic aberrations. Moreover, this 3-D visualization is facile, inasmuch as it does not require troublesome axial changes in the focal plane that normally require complex opto-mechanical devices.

Thus, in effect the invention allows, on-line, "real-time" 3-D movies to be generated of micro-objects that should normally require "virtual" rendering by off-line, convoluted and expensive methodologies.

Utility and Further Advantages of the Invention:

The methods of the invention are implemented with an optical microscope imaging system as e.g. a modified conventional fluorescence microscope being equipped with a two-dimensional camera or with other detector elements being arranged point-wise, as a line or two-dimensionally. In the context of the present invention, "high-resolution imaging" is defined as spatially mapping micro-objects with maximum optical resolution (i.e. on the x,y plane of axes ~100 nm) without recourse to z-axis deflection that should nominally introduce axial aberration and a loss of resolution. A micro-object to be imaged is a biological or synthetic object with a typical cross-section in the range of 1-100 μm. Imaging an object generally comprises mapping of topographical object features. The object features comprise the complete object or only parts thereof, they are located on the surface, or in the volume of the object. The 3-D object shape may be evaluated from the intermediate images, and by grace of the invention specific rotations of the suspended cell, around a fixed xyz coordinate gives optimal optical access to every location within the cell. Thus, the invention makes it possible to generate image planes from different angles and object planes without moving the microscope objective or the scanning table of the microscope. For the application of deconvolution algorithms using PSF based calibrations, this has the added advantage that only a single PSF (measured a fixed distance from the objective and coincident with the focal plane) needs to be applied.

Continuous imaging of controlled changes in position of the object by rotating it around at least one horizontal axis and one vertical axis is very useful for a reduction of the calculation effort required for a three dimensional imaging. A film series (see figures) of cell rotation imaged with a camera at relatively high speed (1-50 images/second) results in a "real" recording of three-dimensional structure, thereby replacing the virtual 3-D rendering generated from conventional opto-mechanical z-stacking acquisition (as described above). Depending on the phase shift of the electric fields at the eight electrodes of the field cage, arbitrary rotational axes can be realized. A rotation of a single cell around two different axes which run through its center—for example within the x,y plane of the microscope's field of view and around the z-axis—enables multiple sets of images to be repeatedly captured and the 3-D structure of the cell can be fully evaluated from all angles, limited only by the number of sampling repeats.

The invention can be combined easily with many different techniques of fluorescence microscopy including all confocal techniques as well as with methods for single molecule detection [e.g. fluorescence correlation spectroscopy, Fluorescence Intensity Distribution Analysis (FIDA), Moment Analysis of Fluorescence Intensity Distribution (MAFID)]. For example, it can be advantageous to move a light beam that passes the objective in one dimension like in a laser-scanning microscope (scanning). The object can be rotated slowly around a horizontal (xy) and/or vertical (z) axis, typically with a frequency of 0.5 rps (revolutions per second) to 1 rpm (revolutions per minute). Along the same lines, a rotation around the z-axis and simultaneous fixed-point scanning in a single direction (like applied in the "In-sight" reader of molecular fluorescence equipped with a linear beam scanner) yields a two-dimensional scan of a plane within the cell. Photon counting and signal processing techniques can then count fluorescent molecules within this specific plane. Along the same lines, the ability of the invention to move the suspended cell along the z-axis is of great utility. In particular, moving the cell eliminates the need to move the carrier in relation to the microscope objective. Thus, once the optical system is aligned for multi color observations, chromatic aberration due to different refractive behavior of different excitation wavelengths in multi color applications does not occur.

The Invention Enhances the Application of Existing 3-D Rendering PSF-Based Algorithms.

The ability to rotate a micro object is useful for sampling sub-compartmentalised domains. For example, by grace of the invention, a living cell may be suspended and imaged in its starting position, before being rotated around an axis within the x,y (equatorial) plane by a defined angle (e.g. 180°, 90° or less) and then imaged again in a second position. The same procedure is repeated for an axis perpendicular to the first in the z plane. This repeating procedure provides a series of images of the same cell from different angles which, in principal, can be used to map the whole 3D volume with a resolution and precision being dependent from the number of images and different angles included (see below). In combination with the ability to rotate the micro-object, the invention allows small (50 nm-50 μm) z-axis movements to be achieved. Thus, an object may be rotated and shifted on the z-axis in order to build a series of images from the same sub-volume, but from different views. Clearly, this type of combined rotational/axial manipulation allows objects to be introduced and orientated within the "optimal imaging space" i.e. at a focal plane whereby the application of PSF-based deconvolution and image reconstruction algorithms may be optimised according to corrections intended to minimise spatial and chromatic aberration. Such existing methods must always take into account the coordinates of the optical measurement volume, defined by the position and characteristics of the microscope objective relative to a fixed position sample. When the z-position changes (i.e. the focus is moved) all these parameters (i.e. those determining the PSF and axial volume) change and must be recalculated, re-measured or estimated. Inasmuch as the invention allows for the optical geometry to be fixed, it therefore greatly reduces the errors intrinsic to measurement and application of existing image algorithms used for deconvolution and volume reconstruction from z-stack image series.

The Invention Opens the Way for Development of New Three Dimensional Image Reconstruction Algorithms.

As mentioned in the preceding paragraph, in addition to enhancing the application of existing algorithms, the invention also opens the way for development of image processing algorithms previously applied to other problems. For example, in X-ray computer tomography objects are imaged by rotation of the detection system around the object. By taking a multiple image series of intermediate coordinates from around the object, it is possible to both render the object's three-dimensional volume, and increase resolution of the images. Thus, by extrapolation, it is in principal possible to apply an analogous algorithmic approach to rendering of micro-object rotational series generated using the invention described here (e.g. see Appendix I). As such, the invention underlies development of completely new "3D Image Reconstruction" methods. The primary advantage of this sort of approach is that the invention ensures that imaging uses solely the x,y plane of resolution to visualize a micro object from multiple view points. Given the absence of axial aberration and reduced z-axis sampling resolution, these new methods shall implicitly deliver 3D reconstruction representations with substantially higher resolution than for conventional reconstruction techniques. Indeed, such methods may also be combined with those already existing image algorithms techniques that use a combination of PSF and volume rendering.

Another subject of the invention is a device for high-resolution imaging of at least one object, which comprises an optical-microscopic imaging system with a receptacle for accommodating the object and a control circuit for controlling the generation of the intermediate images, wherein this imaging system is equipped with a driving device for moving the object relative to the receptacle. According to a preferred embodiment of the invention, the receptacle is provided by a fluidic microsystem with an arrangement of microelectrodes, wherein the driving device comprises the driving electrodes and a driving circuit within the control circuit.

According to a preferred embodiment of the invention, the control circuit contains a switching box being adapted for predetermined switching the rotation axis of the object. The switching box allows predetermined manipulations of the object as well as the implementation of a time trigger.

Further advantageous embodiments of the imaging system are characterized by a multi-electrode arrangement in the fluidic microsystem. The multi-electrodes arrangement comprises e.g. at least 3 electrodes within one plane surrounding the object. These electrodes can be controlled for an improved compensation of position or velocity variations of asymmetric objects.

Further advantages are derived from the fact that the object manipulation in the receptacle does not effect the object (e.g. the physiology of biological cell). High-resolution imaging according to the invention can be conducted even over a long period of time (e.g. 60 minutes).

ALTERNATIVE EMBODIMENT

The implementation of the invention is not restricted to the application with a microscope. Alternatively, the Method for high-resolution image recording of at least one object can be implemented with a measuring device comprising a predetermined measurement field. As an example, the measuring device can comprise an impedance measurement device and said measurement field being the receptacle itself.

4) BRIEF DESCRIPTION OF THE DRAWINGS

Further details and advantages of the invention are described in the following with reference to the attached drawings, which show in.

5) PREFERRED EMBODIMENTS OF THE INVENTION

Firstly, examples of a method according to the present invention are described with reference to FIGS. 1 to 5. For illustrating the reference directions, FIG. 1 shows a site view of an object to be investigated (e.g. a biological cell) in a receptacle of an imaging system and the position of the electrodes at the receptacle, respectively.

Figure 1:
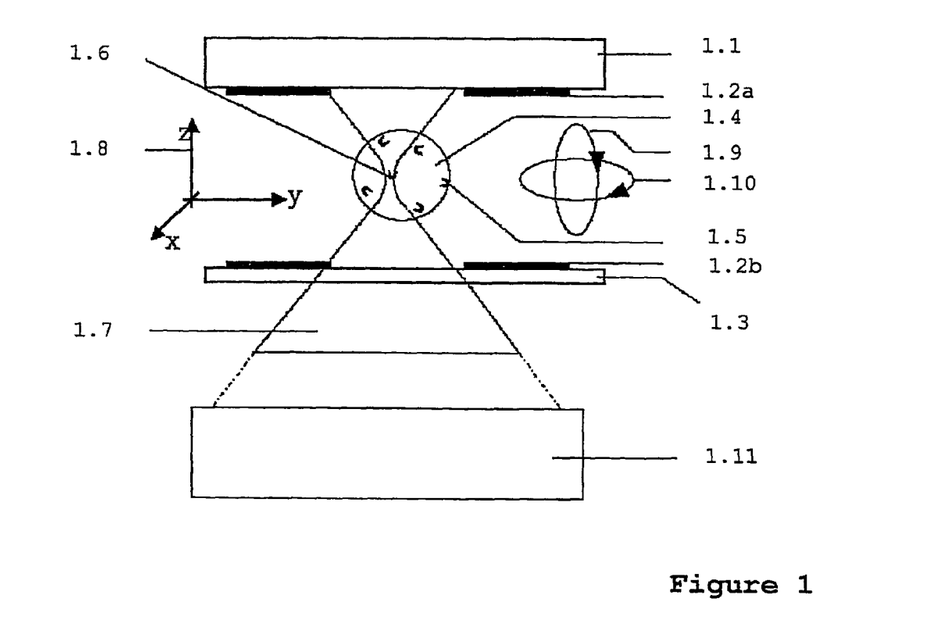
FIG. 1 a schematic view of an object in a receptacle.

FIG. 1 shows the cell 1.4 containing a fluorescent feature 1.5. The cell is caged within the field cage in between the upper glass substrate 1.1 carrying the upper electrode plane 1.2*a* and the lower glass substrate 1.3 carrying the lower electrode plane 1.2*b* by means of the electric field. The cell is rotated around a horizontal axis (1.9) and/or a vertical axis (1.10). It is imaged through a microscope objective lens 1.11 using light of a specific wavelength 1.7 which is focused to a focal volume element 1.6. x, y and z axes of the optical set-up are indicated in perspective view (1.8).

Figure 2:
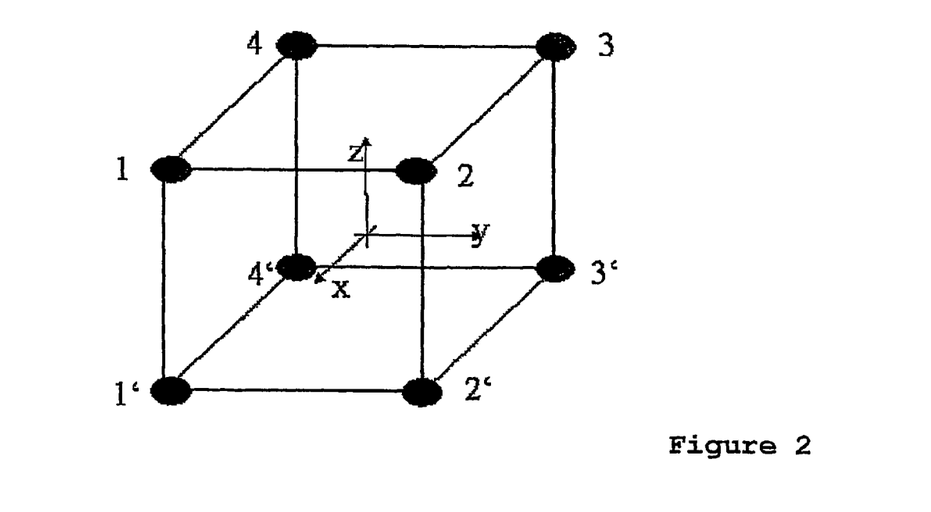
FIG. 2: an arrangement of microelectrodes.

The position of the electrodes of the dielectric field cage is illustrated in FIG. 2. Reference numerals 1, 2, 3, 4 refer to electrode tips of the four electrodes within the upper electrode plane, i.e. on the upper glass substrate of the DFC channel.

Reference numerals 1', 2', 3', 4' refer to electrode tips of the four electrodes within the lower electrode plane, i.e. on the lower glass substrate of the DFC channel which is facing towards the microscope objective. X, y and z are the axes of the optical set-up as described in the text.

Continuous Sampling

Figure 3:
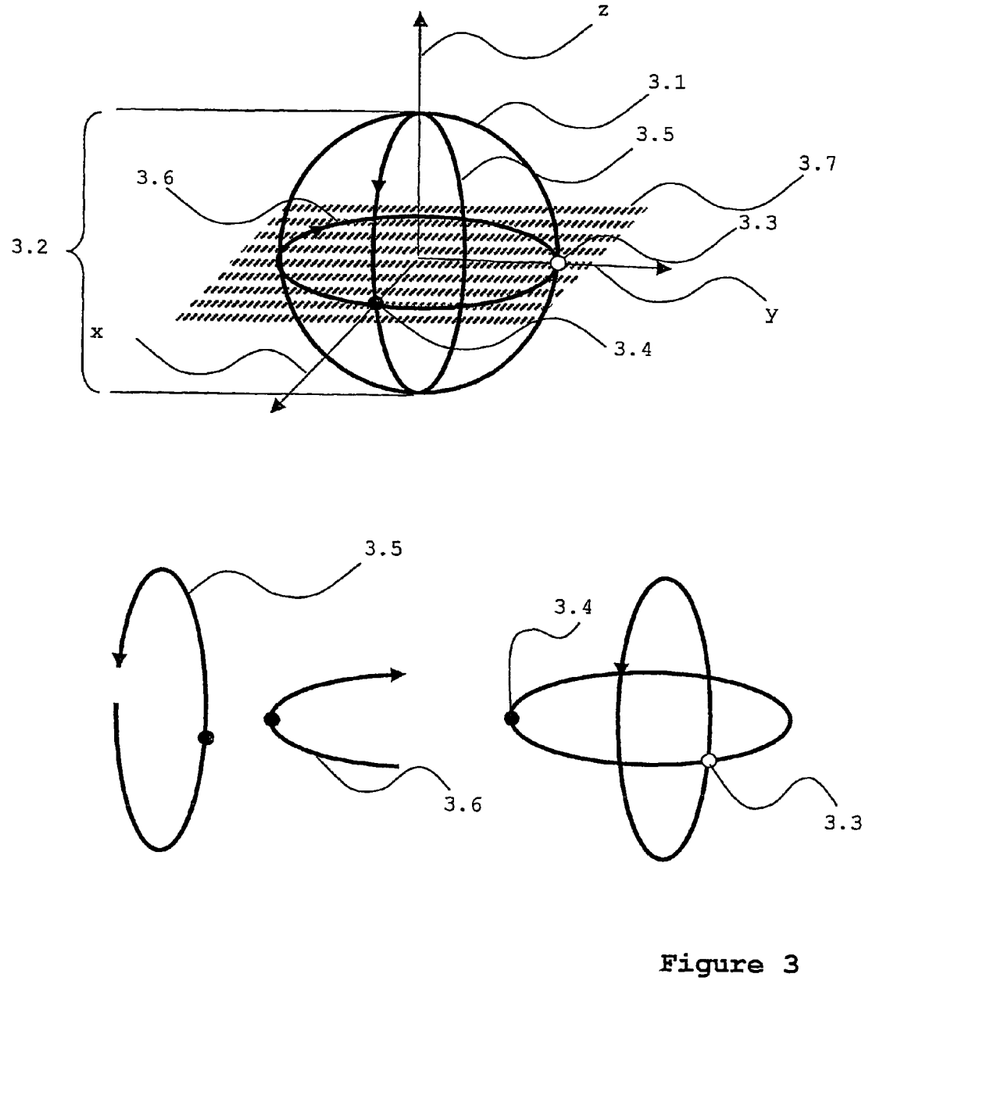
FIG. 3: an illustration of sampling and generation of image-spin series according to the invention.

The method of the invention is based on the collection (sampling) of at least two intermediate images of the object. Sampling can be performed in a continuous fashion as described with reference to FIG. 3. Sampling is achieved by spinning the object for the generation of image-spin series. The cell is rotated at a constant speed of typically 0.1-60 (e.g.

approximately 1) rotation per minute and data sets (intermediate images) are acquired at a speed of typically 1-1000 (e.g. 10) frames per second.

The cell 3.1, having a dimension 3.2 of several micrometers, is continuously sampled during low velocity, high precision rotation of the cell within the z-plane 3.5, i.e. around the y-axis (y). Every feature (e.g. 3.3) of the cell will be within the focal plane 3.7, having a thickness of several hundred nanometers, at a certain time and will be imaged there with highest xy resolution. Discontinuous sampling (see below), i.e. a xy move of 90° (3.6) followed by a second rotation of the cell within a the z-plane (3.5) allows full sampling. This positions a feature with the start position 3.3 for the first scan to the start position 3.4.

Discontinuous Sampling

Figure 4:
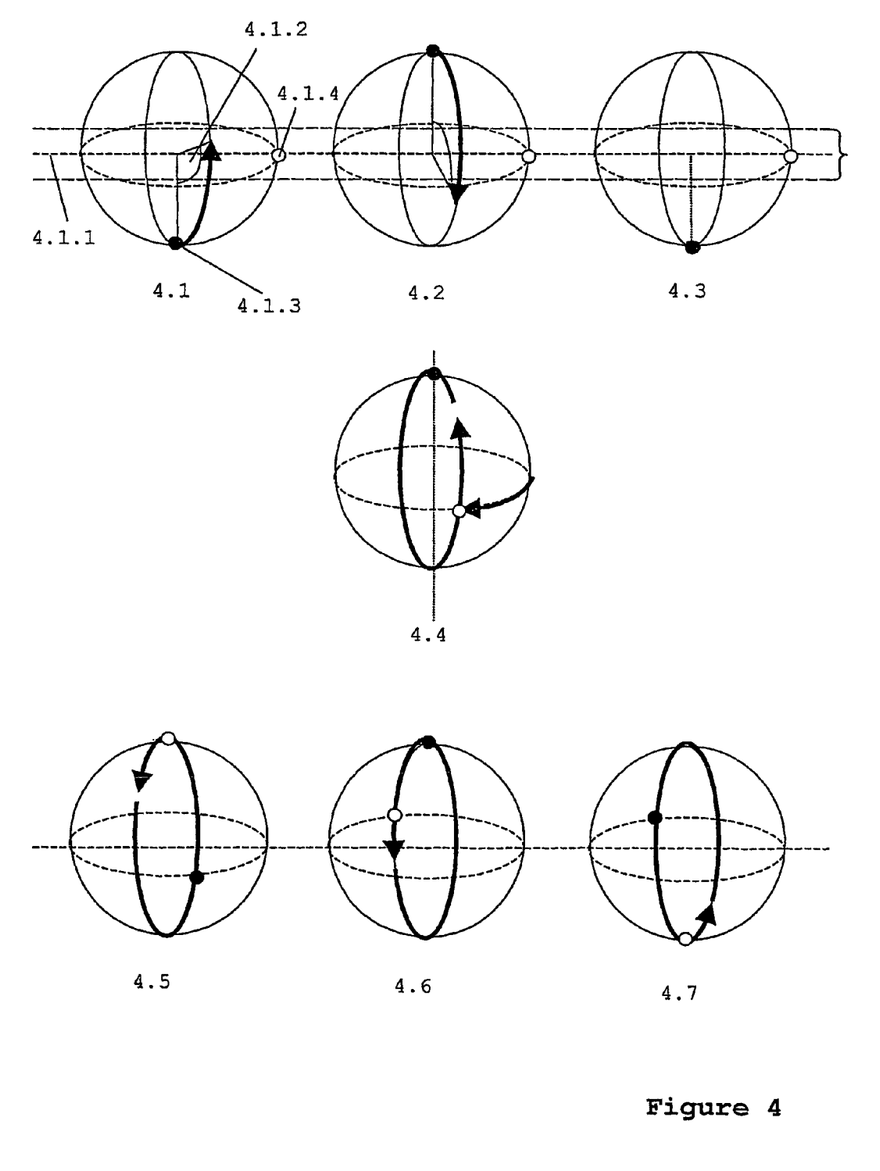
FIGS. 4, 5: further illustrations of object movements in a receptacle.

Examples of discontinuous sampling are illustrated in FIG. 4. The discontinuous sampling is characterized by a series, or some combination therein, of moves comprising rotations and/or z-deflections (4.4) to discrete points where an aimage is captured, or a rotational image scan is initiated. FIG. 4 shows an example of scanning using multiple rotations. A scan is started at t=0 sec. at position 4.1 with a cell rotation speed of approximately 1 rotation per minute and data acquisition speed of 10 frames per second. The cell is spun around the spin axis (4.1.1) by the angle (4.1.2). The cell is rotated by 180° to position 4.2 and 360° to position 4.3. The feature 4.1.3 has then fulfilled the full circle and the feature 4.1.4 has been sampled twice from two distinct positions. The 90° rotation to position 4.4 is preferably conducted by a switching box being a part of the control circuit described below (see FIG. 6)

Figure 5:
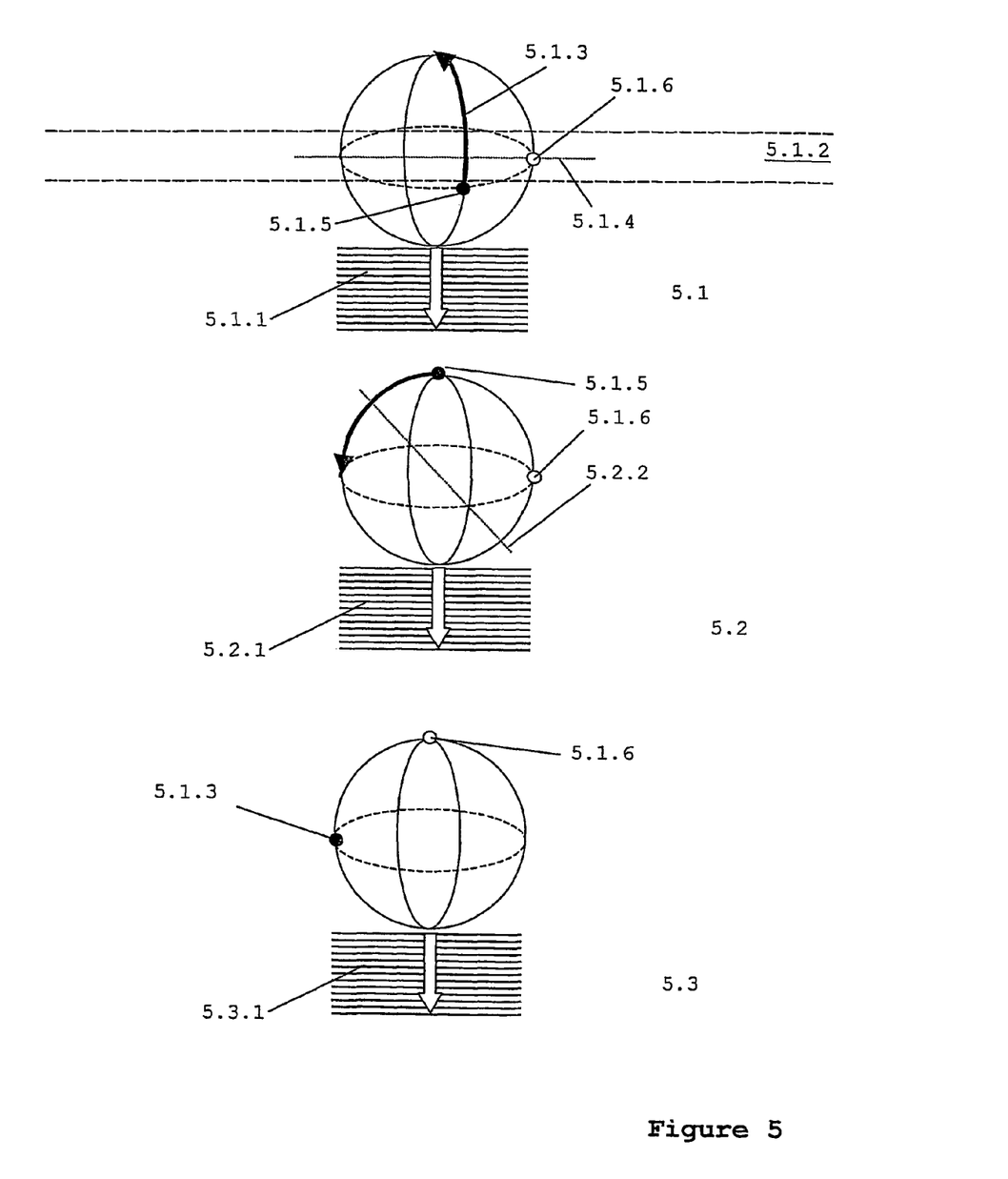

Piezo-Electric Objective Sampler in Combination with Fixed Multiple Sampling Angles The image-spin series of the invention can be combined to good effect with fixed and discontinuous sampling in an alternating-mode. FIG. 5 shows the procedures using fixed sampling angles of 90°. According to alternative embodiments, other sampling angles can be used.

First, a z-scan is performed on a motionless cell at fixed position 5.1 using a piezo-electric objective sampler (schematically shown at 5.1.1). The z-position of the focus is varied in small steps, e.g. 0.1 to 1 μm (z-scan). Reference numeral 5.1.2 indicates an example of an actual focal plane. After taking a series of images, the cell is rotated around the y-axis 5.1.4 by a fixed angle of 90° (5.1.3) to position 5.2 followed by another z-scan (5.2.1). A second series of images is taken. A further rotation by 90° around the x-axis 5.2.2 to position 5.3 followed by another z-scan (5.3.1) completes the procedure.

According to the above principle, the feature 5.1.5 is sampled twice in two perpendicular axes. In position 5.1, x-y-images are taken in dependence on z:

5.1: (x,y→z)

After turn 5.1.3, the feature 5.1.5 has a new z-position in the x-y-images:

5.1.3, 5.2: (z→x, y)

Both scans 5.1.1 and 5.2.1 deliver a plurality of images, which allow a calculation of the x,y,z-volume of the feature 5.1.5. The feature 5.1.6 is not sampled until the second turn. The total object is reconstructed from all coordinate stacks after the second rotation around the x-axis only.

Figure 6:
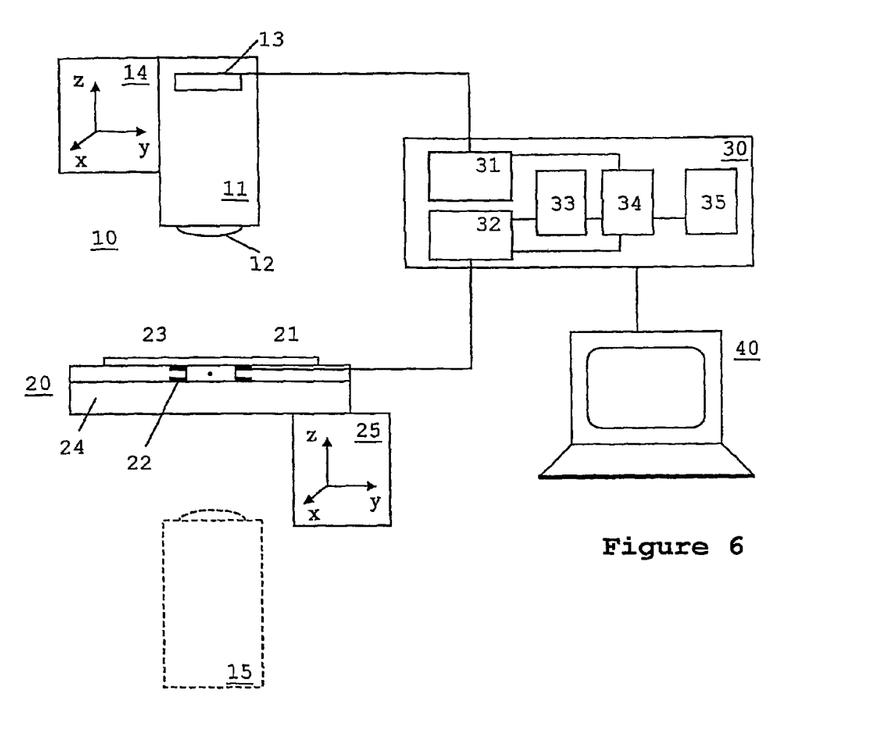
FIG. 6: a schematic view of an imaging system according to the invention.

FIG. 6 illustrates a preferred embodiment of a high-resolution imaging device according to the invention. The imaging device comprises an optical microscope imaging system (10), a receptacle (20) and a control circuit (30). Preferably, the imaging system (10) comprises a conventional optical microscope (11) equipped with a barrel lens (12) objective, and an imaging camera (13). The camera (13) is e.g. a CCD camera. Alternatively, photodiodes or multiplier tubes can be used as detectors. The microscope (11) (shown schematically) can be positioned relative to the receptacle (20) with a microscope drive (14). The sample illumination is conducted through the microscope (11) or (shown with broken lines) with a separate illumination device (15), which can be positioned on the opposite side of the receptacle (20). The arrangement of FIG. 6 can comprise a laser tweezer device (not shown) for additionally exerting optical forces to the object.

The receptacle (20) comprises a fluidic microsystem with a channel or chamber (21) for accommodating a liquid with at least one suspended object to be investigated. Microelectrodes (22) are arranged on the walls of the chamber (21) as it is known from conventional microsystem technology. The chamber (21) is closed with a cover glass (23) and carried by a support (24). The support (24) can be adjusted with a receptacle drive unit (25).

The control circuit (30) comprises a data set storage (31), a parameter storage (32), a switching box (33), a calculation circuit (34) and an object image storage (35). The control circuit (30) is connected with further input/output devices (40), e.g. with a display and a printer.

For conducting the method according to the invention, the object to be investigated is positioned in the optical axis of the microscope (11). The microelectrodes are controlled with a certain set of parameters, which are contained in the parameter storage (32). The parameters comprise e.g. the phase, amplitude and frequency of electrical fields, information about the control mode as well as object properties. According to the parameters, the object is moved within the receptacle (20) as described above. During the movement, a series of at least two data sets is recorded with the camera (13) and submitted to the data set storage (31). The data sets are evaluated in the calculation circuit (34) in dependence on the parameters (32) for obtaining the object image, which is submitted to the object image storage (35).

The switching box (33) is connected with the parameter storage (32) and the calculation circuit (34). The switching box (33) is arranged for submitting predetermined switching parameters to the parameter storage (32). According to the switching parameters, a movement mode of the object in the receptacle (20) is adjusted.

EXAMPLES

Imaging Experiments Performed with a Prototypic Set-Up Based on the Invention

—A—Visualization of the Lamin Structure of HeLa Cells

As an example for studying a cellular protein by live three-dimensional microscopy fluorescent nuclear lamin proteins inside a live suspended cell were imaged using a prototype of the invention.

Lamins are the major components of the nuclear lamina, a two-dimensional filamentous network at the periphery of the nucleus in higher eukaryotes, directly underlying the inner nuclear membrane. In the course of cell-cycle-dependent dynamics of the nucleus in higher eukaryotes, lamins as well as lamin-binding proteins seem to possess important functions during various steps of post-mitotic nuclear reassembly and seem to play a role in various pathological processes in muscle (Emery-Dreifuss muscular dystrophy, EDMD; dilated cardiomyopathy and conduction system defect, DCM-CD; and limb-girdle muscular dystrophy, LGMD) and adipose tissue (Dunnigan-type familial partial lipodystrophy, FPLD). Lamins are more dynamic than originally thought. These findings altogether demonstrate the necessity to investigate the localization of lamins within the cell and their dynamics with great precision in order to learn about their functions and dysfunctions. HeLa cells were used for this purpose which overexpressed lamin protein fused to the fluorescent protein dsRed.

The cells were detached from the culture flask using trypsin and suspended in Cytocon™ Buffer II containing 30 mM salt/phosphate buffer balanced to normo-osmolar values using 0.3 M inositol solution. The cells were introduced into DFC4 chips and caged within the 30 µm field cage (distance between opposing electrode tips within one plane: 30 µm) using the Cytocon™ 300. The field cage was energized at 700 kHz and 1.9-2.6 Vrms. The cells were subjected to a rotational movement by using the "rot II" mode of the Cytocon™ 300. The DFC4 Chips was mounted on a Zeiss Axiovert 200 microscope equipped with the Photometrics Cool SNAP camera Hamamatsu and the T.I.L.L. Vision imaging system. The cell rotated at a constant speed of approximately 20 revolutions per minute and an image-spin series was generated at a speed of 10 frames per second with 50 ms exposure time. The axis of the rotation was selected by a controlled modulation of amplitudes of the upper and lower electrode plane of the field cage.

Figure 7:
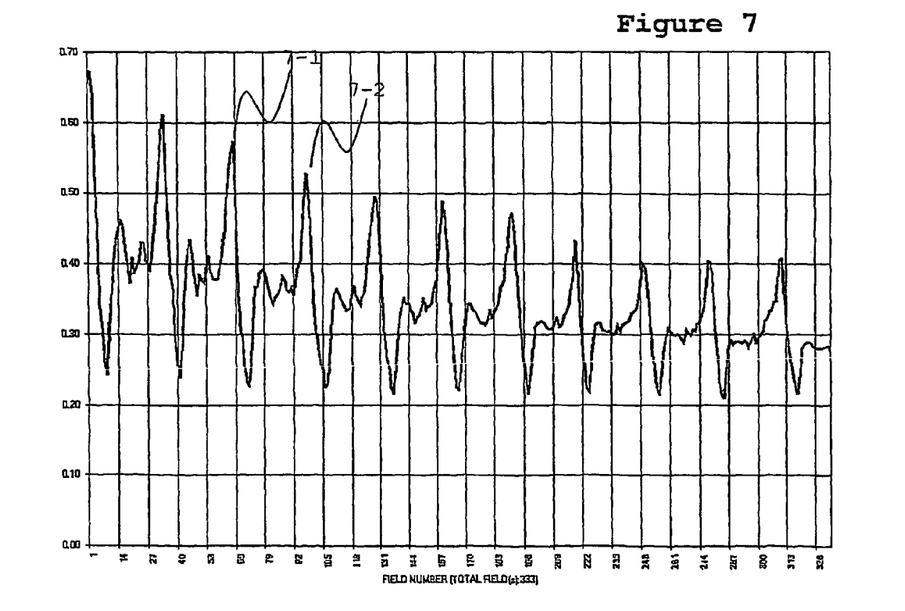
FIGS. 7, 8: illustrations of experimental results.

FIG. 7 shows a diagram of fluorescence intensity within an image area of the HeLa cell during the image-spin series of the experiment described here and partially shown below in FIG. 9. The fluorescence intensity in arbitrary units is plotted against the number of the images taken at a rate of 10 per second. The position of the peaks demonstrate the accuracy of the frequency which can be achieved for a cell spin. The period can be determined from the distance of two peaks, e.g., between peak 7-1 and 7-2.

Figure 8:
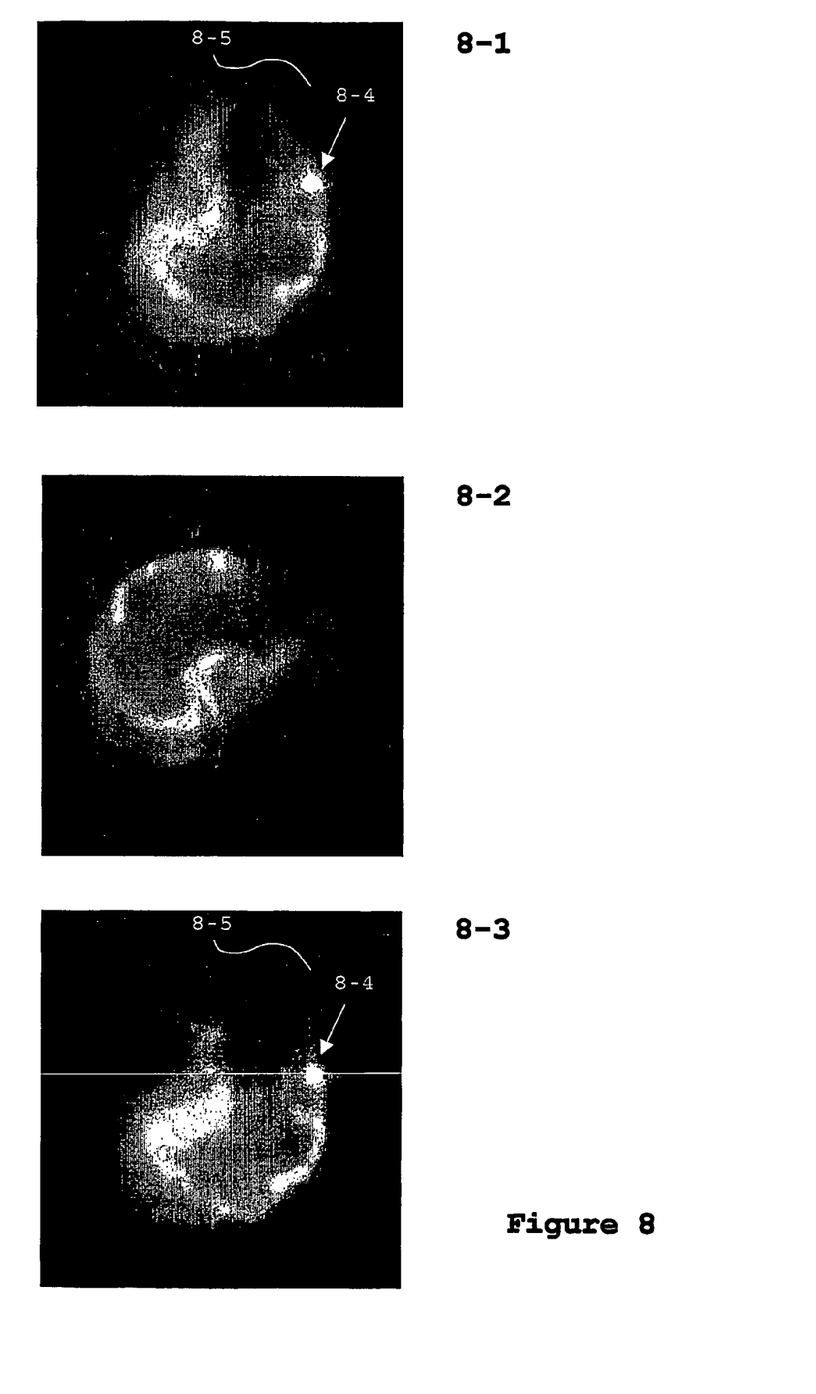

Image-spin series of the HeLa cell with overexpressed lamin protein fused to the fluorescent protein dsRed are illustrated in FIG. 8. FIG. 8-1 show the image taken at second 4, FIG. 8-2 is the image taken at second 21 and FIG. 8-3 is the image taken at second 34. The fluorescent object 8-4 occurs in image 8-1 at a specific position given by a xy-coordinate 8-5 and it appears at an identical position in the image 8-3 after ten revolutions.

—B—Rotation of Jurkat Cells Around Two Different Rotation Axes

Jurkat-cells were suspended in Cytocon™ Buffer II and introduced into a DFC Chip. A single cell was caged within the center 30 µm field cage of the chip using a Cytoman™ and a frequency of 700 kHz and an amplitude of 1.9-2.6 Vrms. The cell could be continuously rotated around a horizontal as well as a vertical axis without altering its center position. Spin frequency could be varied from 0.01 rps (revolutions per second) to 0.5 rps by altering the amplitude in a range of 1.5-3 Vrms and/or the frequency in a range of 0.3 MHz-8 MHz.

The Cytoman™ provides two different rotational field modes and one alternating field mode according to table 1. A switch box enabled to change between two different spin axes (around a vertical and a horizontal spin axis, see FIG. 2).

TABLE 1

Addressing of the eight DFC electrodes for a cell spin around a vertical and a horizontal axis as well as for motionless positioning (no rotation). The phase shift of the field vector is given (Schnelle, Th. et al. "J. Electrostatics" 50, 2000, 17-29).

| | | Electrodes | | | | | | | |
|---|---|---|---|---|---|---|---|---|---|
| | | 1 | 2 | 3 | 4 | 1' | 2' | 3' | 4' |
| Vertical spin axis (z) | Rotational field I | 0 | $\pi/2$ | $\pi$ | $-\pi/2$ | $\pi$ | $-\pi/2$ | 0 | $\pi/2$ |
| Horizontal spin axis (x, y) | Rotational field II | 0 | $\pi/2$ | $-\pi/2$ | $\pi$ | $-\pi/2$ | $\pi$ | 0 | $\pi/2$ |
| Fixed position | Alternating field, type C | 0 | $\pi$ | 0 | $\pi$ | 0 | $\pi$ | 0 | $\pi$ |

APPENDIX I

A deconvolution, volume reconstruction operation bases itself on the following considerations: "A digital image (e.g. microscopic image of a distribution of fluorescent molecules) is a convoluted 2-dimensional representation of a 3-dimensional reality. The individual information given at each image pixel includes not only the true signal emerging from a single point in the focal plane, but also varying degrees of additional signal accumulated from fluorescent out-off-focus volumes, above and below the focal plane, but within the focal depth along z-axis" (from Shorte & Bolsover, 1999). Fluorescent specimens act as self-luminous objects in which point sources behave as independent sources. Neglecting the light scattering, the optical density g at each pixel can be written as:

$$g = \int Hc\, dz$$

wherein H is the extinction coefficient and c the absorber concentration. For reconstructing a 3-dimensional image of the object, c is to be obtained from entities g and H for a plurality of image planes by deconvolution.

The deconvolution is obtained in analogy to conventional reconstruction from radiographic projections (tomography). In standard tomography, the specimen does not move but the radiographic apparatus turns around it to get a set of images. The values c can be reconstructed as described by B. Chalmond et al. in "inverse problems", vol. 15, 1999, p. 399-411. According to the present invention, the situation is reversed. The object to be investigated is rotated whereas the microscope is fixed. The conventional tomography algorithms can be used after a numerical coordinate transformation of the microscope set up into the radiographic context.

The invention claimed is:

1. A method for high-resolution image recording of at least one object with a microscope, comprising the steps of:
    positioning the at least one object in a receptacle arranged in an optical axis of the microscope,
    generating at least two first data sets per object, wherein:
    (a) the at least two first data sets represent intermediate images of the at least one object with at least two different predetermined orientations relative to the optical axis of the microscope, (b) the at least two different predetermined orientations of the object are provided by controlled movement of the at least one object relative to the receptacle, and (c) the controlled movement comprises a rotation of the at least one object by an influence of electrical field forces, said object being rotated around at least one of a predetermined axis and a predetermined rotation angle, and evaluating the data sets to obtain quantitative three-dimensional information of the at least one object, wherein said quantitative three-dimensional information represents a three-dimensional shape of the at least one object.

2. The method according to claim 1, wherein said moving of the at least one object relative to the receptacle further comprises a translation of the at least one object by the influence of the electric field forces.

3. The method according to claim 2, wherein said rotation comprises at least one rotation with a rotation axis parallel to the optical axis.

4. The method according to claim 2, wherein said rotation comprises at least one rotation with a rotation axis slanted relative to the optical axis.

5. The method according to claim 4, wherein said rotation axis is slanted within an angle range of up to 90°.

6. The method according to claim 2, wherein said rotation comprises:
   a rotation in a continuous mode or for predetermined time periods and angles, and/or
   a rotation with changing rotational axes.

7. The method according to claim 2, wherein said rotation is conducted by holding the at least one object at a fixed position by said electric field forces and by rotating the at least one object by optical forces.

8. The method according to claim 1, further comprising steps of generating further intermediate images of the object, each with another focal plane, respectively, wherein each said focal plane is adjusted by scanning an objective of the microscope parallel to the optical axis.

9. The method according to claim 8, wherein said at least two different predetermined orientations of the object and said scanning an objective are conducted in an alternating mode.

10. The method according to claim 1, wherein said positioning comprises suspending said at least one object in a liquid in said receptacle.

11. The method according to claim 1, wherein said step of evaluating the data sets comprises at least one step selected from the group consisting of removing out-of-focus light and reconstructing a three-dimensional map/image of the at least one object.

12. The method according to claim 1, wherein said at least one object comprises at least one eukaryotic cell, at least one prokaryotic cell and/or at least one artificial particle.

13. The method according to claim 1, wherein said microscope is used as a fluorescence microscope, a phase contrast microscope, a differential interference contrast microscope or a confocal microscope.

14. An imaging device for high-resolution image recording of at least one object, comprising:
   a microscope imaging system with an optical axis,
   a receptacle for accommodating said at least one object, said receptacle being arranged in said optical axis, and
   a control circuit being arranged for: (a) generating at least two first data sets per object, wherein said at least two first data sets represent intermediate images of the at least one object with at least two different predetermined orientations relative to the optical axis, (b) providing controlled movement of the at least one object relative to the receptacle to generate the at least two different predetermined orientations, wherein the controlled movement comprises a rotation of the at least one object by an influence of electrical field forces, said object being rotated around at least one of a predetermined axis and a predetermined rotation angle, and (c) evaluating the data sets to obtain an object image representing a three-dimensional shape of the at least one object, and
   a driving device adapted to controllably move the at least one object relative to the receptacle.

15. The imaging device according to claim 14, wherein said receptacle comprises a chamber of a fluidic microsystem and said driving device comprises microelectrodes arranged at walls of said chamber and connected with said control circuit.

16. The imaging device according to claim 15, wherein said driving device comprises at least three microelectrodes arranged in one plane in said chamber.

17. The imaging device according to claim 16, wherein said driving device comprises at least six microelectrodes arranged in two planes in said chamber.

18. The imaging device according to claim 14, wherein said control circuit comprises a switching box arranged for switching a rotation axis of the at least one object.

19. A method for high-resolution image recording of at least one object with a measuring device with a predetermined measurement field, comprising the steps of:
   positioning the at least one object in a receptacle arranged in the measurement field of the measuring device,
   generating at least two first data sets per object, wherein:
   (a) the at least two first data sets represent intermediate data of the at least one object with at least two different predetermined orientations relative to the measurement field of the measuring device, (b) the at least two different predetermined orientations of the object are provided by controlled movement of the at least one object relative to the receptacle, and (c) the controlled movement comprises a rotation of the at least one object by an influence of electrical field forces, said object being rotated around at least one of a predetermined axis and a predetermined rotation angle, and
   evaluating the data sets to obtain quantitative three-dimensional information of the at least one object, wherein said quantitative three-dimensional information represents the three-dimensional shape of the at least one object.

20. The method according to claim 19, wherein said measuring device comprises a microscope and said measurement field is an optical axis of the microscope.

21. The method according to claim 19, wherein said measuring device comprises an impedance measurement device and said measurement field is the receptacle.

* * * * *